United States Patent [19]

Moriya et al.

[11] Patent Number: 5,599,999
[45] Date of Patent: Feb. 4, 1997

[54] PROCESS FOR PREPARATION FOR ALKANOLAMINE, CATALYST USED IN THE PROCESS AND PROCESS FOR PREPARATION OF THE CATALYST

[75] Inventors: Atusi Moriya, Yokohama; Hideaki Tsuneki, Tokyo, both of Japan

[73] Assignee: Nippon Shokubai Co., Ltd., Osaka, Japan

[21] Appl. No.: 333,329

[22] Filed: Nov. 2, 1994

[30] Foreign Application Priority Data

Nov. 2, 1993 [JP] Japan ................................ 5-295992
Nov. 2, 1993 [JP] Japan ................................ 5-295993

[51] Int. Cl.$^6$ ................................................ C07C 209/16
[52] U.S. Cl. .......................................... 564/477; 564/475
[58] Field of Search ................................ 564/475, 476, 564/477

[56] References Cited

U.S. PATENT DOCUMENTS

| | | | |
|---|---|---|---|
| 4,438,281 | 3/1984 | Johnson, Jr. | 564/477 |
| 5,102,849 | 4/1992 | Kemp et al. | 502/214 |
| 5,210,325 | 5/1993 | Kemp et al. | 568/618 |
| 5,395,973 | 3/1995 | Washington et al. | 564/475 |

FOREIGN PATENT DOCUMENTS

| | | |
|---|---|---|
| 0250168 | 12/1987 | European Pat. Off. . |
| 0375267 | 6/1990 | European Pat. Off. . |
| 0539821 | 10/1992 | European Pat. Off. . |
| 49-47728 | 12/1974 | Japan . |
| 2225446 | 9/1990 | Japan . |
| 158167 | 3/1957 | Sweden . |

OTHER PUBLICATIONS

Industrial and Engineering Chemistry, Product Research and Development, (1986), 25:424–430.

"Ion–Exchange—Introduction on Theory and Practice", (1981), Maruzen Co., Ltd., p. 34.

*Primary Examiner*—Brian M. Burn
*Attorney, Agent, or Firm*—Sherman and Shalloway

[57] ABSTRACT

A process is provided which comprises using a catalyst comprises a rare earth element supported on an inorganic heat-resisting carrier, when a monoethanolamine is selectively prepared by reacting an alkylene oxide with ammonia in a liquid phase. This catalyst has excellent monoalkanolamine selectivity and heat resistance; and therefore, even when the ratio of ammonia to the alkylene oxide is lower compared with cases where other catalysts are used, an equal or more amount of the monoalkanolamine can be formed, and thus the recovery cost of the unreacted ammonia is reduced. Further, since the total amount of the feed raw materials is reduced, apparatuses for the reaction system and recovery system can be made smaller, and thus the cost of equipment is reduced.

13 Claims, No Drawings

PROCESS FOR PREPARATION FOR ALKANOLAMINE, CATALYST USED IN THE PROCESS AND PROCESS FOR PREPARATION OF THE CATALYST

This invention relates, in preparation of an alkanolamine by amination of an alkylene oxide with ammonia using a catalyst carrying a rare earth element, to a process to prepare a monoalkanolamine selectively and with good productivity and with lowered formation of compounds in which two moles or more of the alkylene oxide are bound (particularly, compounds in which 3 moles or more thereof are bound). The process of this invention is particularly useful in industrial preparation of ethanolamines by amination of ethylene oxide with ammonia. This invention also relates to the catalyst and a process for preparation of the catalyst.

As a process of preparing an alkanolamine by amination of an alkylene oxide with ammonia is industrially carried out a process to prepare an ethanolamine by reacting ethylene oxide with aqueous ammonia (ammonia concentration: 20–40% by weight). Diethanolamine and triethanolamine are produced as by-products other than monoethanolamine according to this process, but the demand for triethanolamine among them is now decreased, and therefore it is needed to suppress the formation of triethanolamine. Thus, reaction is, usually, carried out with largely excess ammonia such that the mole ratio of ammonia to ethylene oxide is on the order of 3 to 5, but nevertheless the selectivity of triethanolamine is 10 to 20% by weight or more and the selectivity of monoethanolamine is 50% by weight % or less.

On the other hand, in a system of absence of water an alkylene oxide and ammonia scarcely react. Thus, in such reaction, the presence of a catalyst is requisite, and homogeneous catalysts are proposed such as, for example, organic acids, inorganic acids and ammonium salts (Swedish Patent No. 158,167). However, these homogeneous catalysts have their problem in separation of the catalyst, and their performance is not sufficient, either. As an attempt to immobilize such a homogeneous catalyst is proposed an ion exchanger resin comprising a resin having immobilized therein sulfonic acid groups (Japanese Patent Publication No. 47728/1974). This catalyst has comparatively good activity and selectivity and is industrially used. However, the ion exchange resin has a problem that its maximum use temperature is low. Usable maximum temperature for usually available ion exchange resins is rather as low as on the order of 120° C. (see "Ion-Kokan-Riron to Oyo heno Tebiki" (Ion Exchange-Introduction on Theory and Practice), cotranslated by Rokuro KURODA and Masami SHIBUKAWA, published in 1981 by Maruzen Co., Ltd., page 34), and thus when ethylene oxide and ammonia are reacted at a low mole ratio of the latter to the former, problems arise that the temperature of the catalyst layer goes beyond the heat resisting temperature due to the heat of reaction, and long-term use thereof under this temperature condition deteriorates the catalyst. Thus it is difficult to make the mole ratio of ammonia to ethylene oxide the order of 20 to 25 or less. Therefore, in order to overcome the drawback of low heat resistance of ion exchange resins, inorganic catalysts excellent in heat stability have been researched. U.S. Pat. No. 4,438,281 discloses that silica alumina, which is generally often used, exhibits activity. Various zeolite catalysts are investigated in comparison with ion exchange resins in Industrial and Engineering Chemistry, Product Research and Development, 1986, volume 25, pages 424–430, but they do not excel the ion exchange resins in selectivity to monoalkanolamines. Further, Japanese Laid-Open Patent Publication No. 225,446/1990 discloses acid-activated clay catalysts. Some of these catalysts exhibit a monoethanolamine yield of as high as 60% by weight or more. However, since none of them are sufficient in the point of selectivity to monoalkanolamines, it is necessary to carry out the reaction at a mole ratio of ammonia to ethylene oxide of 20 to 30 or more, and thus the cost of equipment for recovery and recycle use of ammonia becomes large.

The object of this invention lies in providing a catalyst having high heat resistance and high selectivity, by use of which the mole ratio of ammonia to an alkylene oxide can be lowered up to a practically advantageous level, and even at the level an alkanolamine can be prepared selectively; a process of preparing an alkanolamine using this catalyst; and a process of preparing this catalyst.

The present inventors have vigorously studied for solving the above problems; as a result have found that a catalyst comprising a rare earth element supported on an inorganic heat-resisting carrier exhibits excellent performance; and have completed this invention.

Thus, according to this invention there is provided a process for preparation of an alkanolamine represented by the general formula (II)

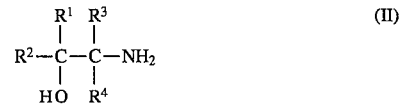

wherein $R^1$, $R^2$, $R^3$ and $R^4$ each independently represent a hydrogen atom, a methyl group or an ethyl group, which comprises reacting an alkylene oxide represented by the general formula (I)

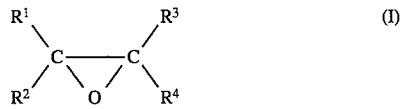

wherein $R^1$, $R^2$, $R^3$ and $R^4$ are the same as in the general formula (II), with ammonia in a liquid phase in the presence of a catalyst comprising a rare earth element supported on an inorganic heat-resisting carrier. According to this invention there is further provided a catalyst for preparation of alkanolamines which is used in preparation of the alkanolamine represented by the general formula (II)

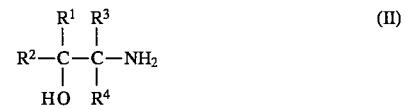

wherein $R^1$, $R^2$, $R^3$ and $R^4$ and each independently represent a hydrogen atom, a methyl group or an ethyl group, by reaction of an alkylene oxide represented by the general formula (I)

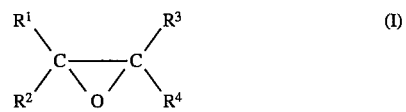

wherein $R^1$, $R^2$, $R^3$ and $R^4$ are the same as in the general formula (II), with ammonia in a liquid phase; the catalyst comprising a rare earth element supported on an inorganic heat-resisting carrier.

Since the catalyst of this invention is superior or to solid catalysts so far known in selectivity to monoalkanolamines and has higher heat resistance than ion exchange resins, it is possible to lower the mol ratio of ammonia to an alkylene oxide, and the reaction can be carried out industrially advantageously.

A rare earth element is used as the active component of the catalyst of this invention. As the rare earth element can be used lanthanoid elements (lanthanum, cerium, praseodymium, neodymium, samarium, europium, gadolinium, terbium, dysprosium, holmium, erbium, thulium, ytterbium and lutetium), scandium or yttrium.

As raw materials of the rare earth elements, any ones can be used so long as they become insoluble in the reaction solutions by the heat treatment during the catalyst preparation steps, and particularly can be used nitrates, sulfates, carbonates, acetates, oxalates, heteropolyacid salts, phosohates, halides, oxides hydroxides, etc. of the elements.

As the carrier in the catalyst of this invention, any one can be used so long as it is an inorganic heat-resisting carrier having specific surface area of 1 to 500 $m^2/g$. Known various carriers can be used, for example natural products (diatom earth, pumice, clay, etc.), simple oxides (silica, alumina, titania, zirconia, etc.), compound oxides (silica alumina, titania silica, zirconia silica, perovskite, etc.), inorganic refractories (silicon carbide, silicon nitride, graphite, etc.), inorganic ion exchanger (SAPO, MeAPO, metallosilicates, layered silicate salts, etc.), etc.

As processes for the carriage can be used an ion exchange process, an impregnation process, a kneading process, etc.

The impregnation process is a carriage process which comprises putting a molded carrier in a solution of a soluble rare earth element, and removing the solvent with heating.

The kneading process is a process which comprises adding to powder of a carrier a rare earth element compound to be supported, sufficiently kneading the mixture with a small amount of a solvent in a kneader, and molding the resultant cake.

The ion exchange process is a carriage process which comprises putting a carrier in a solution of a soluble rare earth element, ion exchanging the alkali ion, etc. at the exchange site of the ion exchanger for the rare earth element, and then separating the ion exchanger from the solution. In order to uniformly carry a rare earth element on a carrier, the ion exchange process is convenient. An inorganic ion exchanger is used as the carrier in the ion exchange process. The inorganic ion exchanger includes, for example SAPO, McAPO, metallosilicates, layered silicate salts, etc.

SAPO is a substance comprising crystalline aluminum phosphate (AlPO) having substituted silicon for part of the phosphorus, or a substance comprising AlPO having substituted two silicons for one pair of the aluminum and phosphorous. MeAPO is a substance comprising AlPO having substituted for the aluminum a metal element other than silicon (Co, Mg, Mn, Zn, Fe or the like). They each have an ion exchange site, and SAPO-5, -11, -17 and -40, MAPO (Mg) -5, -11 and -36, MnAPO-5 and -11, CoAPO-5 and -36, FAPO (Fe)-34, ZAPO (Zn)-34, etc. are known (the - numbers are the same discrimination number as in AlPOs of the corresponding structures).

The metallosilicate is a substance which comprises crystalline silicate having substituted a metal for the silicon, and has very uniform pores, and therein the balance of electric charge is lost in the same extent as the number of the metal substituted for the silicon, and thus ion exchange sites exist. As the metallosilicates are specifically often used crystalline aluminosilicates known as zeolites. As the zeolites can generally be used A-type, X-type, Y-type, L-type and pentacyl-type (ZSM-5, ZSM-11, etc.) zeolites, mordenite, ferrierite, etc. Other metallosilicates include iron silicate, nickel silicate, etc.

As the layered silicate salts are known smectite silicate salts, and specifically used are montmorillonite, saponite, hectorite, nontronite, etc. These silicate salts have ion exchange sites, ions of alkali metals such as sodium usually occupy these sites, and these layered silicate salts are often basic.

In the preparation processes other than the kneading process, soluble salts (nitrates, halides, salts of heteropolyacids, etc.) can be used as raw materials for the catalysts.

The carriage rate varies depending on the surface area of the carrier and the kind of the rare earth element, etc., but is usually in the range of 0.5 to 50% by weight, preferably 1 to 30% by weight.

When rare earth element is supported by the ion exchange process, it is not always necessary to high temperature treat the resultant product, but a desired catalyst can usually be obtained by high temperature treating the product in the range of 300° to 700° C. The high temperature treatment is usually carried out in the air, but where oxidation treatment is not particularly required, the thermal decomposition of the raw materials for the catalyst can be carried out in an atmosphere of an inert gas such as nitrogen or in vacuum.

There is no particular limitation about the particle size of the catalyst of the invention, and those having average particle sizes which have so far conventionally been used can be used.

As to the particle sizes of catalysts, it is known that, in general, when a catalyst having a small average particle size is packed into a reactor having a height of the order of 1 to 5 m and reaction is carried out, the pressure loss become as high as 3 to 50 MPa and a large difficulty is brought about as a practical matter; it is necessary for prevention thereof to mold the catalyst having a particle size of 0.3 mm or more; and there arises a problem of lowering of catalyst performance in the catalyst having such a particle size. However, as to the catalyst of the invention, where the catalyst is a catalyst which comprises an inorganic heat-resisting carrier having carried thereon a rare earth element, and in which catalyst the volume of pores having a pore size of 10 nm to 10 µm is 0.2 to 1 $cm^3/g$, a problem as above-mentioned does not arise even if the average particle size of the catalyst is 0.3 mm or larger (the average particle size of the catalyst not spherical, i.e. the equivalent particle size, is assumed to mean the diameter of a sphere having the same outside surface area as in the catalyst). Such a catalyst of the invention can be prepared by mixing a raw material for the catalyst, comprising the carrier having carried thereon a rare earth element, with a pore-forming agent in an amount of 20 to 200% by weight based on their dry weight; molding the mixture into moldings having an average particle size of 0.3 mm or larger; and then high temperature treating the moldings to burn and remove the poreforming agent. The catalyst of the invention can also be prepared by making the carrier in which the volume of pores having a pore size of 10 nm to 10 µm is 0.2 to 1 $cm^3/g$, carry a rare earth element. The range of the above pore volume with respect to the catalyst carrying the rare earth element is critical, and where the range is smaller than 0.2 $cm^3/g$, the selectivity and activity of the catalyst is low, and where it is larger than 1 $cm^3/g$, the strength of the catalyst becomes low.

As the pore-forming agent can be used a substance which does not have a bad influence on the performance of the catalyst and can be burned and removed by the high temperature treatment. These pore-forming agents include, for example, various ammonium salts such as ammonium nitrate and ammonium acetate; organic compounds such as urea; nonaqueous organic compounds such as various polymers and fibers; etc. The water insoluble organic compounds can suitably be used in view of the efficiency of pore formation, easiness of molding, etc. As the organic compound, any one can be used so long as it has some extent of hygroscopicity, is composed of fine powder, and can be burned and removed by high temperature treatment of several hundred degree, and crystalline cellulose is particularly preferable in view of handle-ability. As crystalline cellulose can be used powder obtained by pulverizing filter paper, powder obtained by pulverizing pulp, etc. When an organic substance such as crystalline cellulose is used as the pore-forming agent, it cannot be decomposed and removed by simple heating treatment, and therefore can be burned and removed in a gas containing oxygen (it is convenient to use air).

Another metal element having a valence of 2 or more can be added simultaneously in order to utilize the expensive rare earth element and make the preparation of the catalyst easy. As the element to be added, any one can be used so long as it is an element not spoiling the activity and selectivity. These elements include, for example, IVB group elements (Ti, etc.), VB group elements (Nb, etc.), VIB group elements (W, etc.), VIIB group elements (Mn, etc.), VIII group elements (Fe, etc.), III A group elements (Al, etc.) and IVA group elements (Sn, etc.) in the periodic table. Metals having a valence of 3 such as Fe and Al often give desirable results because they have the same valence as in the rare earth element. There is no particular limitation about the amount to be added so long as the amount is such that the effects of the rare earth element is not spoiled, but such an element is usually used in the range of 0 to 10 as an atom ratio to the rare earth element.

In the reaction using a usual acid catalyst, ammonia, which is a comparatively weak inorganic base, cannot be activated; on the other hand, the reactivity of monoethanolamine, which is an amine having an organic active hydrogen, is 5 to 20 times larger than that of ammonia; and therefore, diethanolamine and triethanolamine have been successively formed. On the other hand, when the catalyst of the invention carrying a rare earth element is used, ammonia as an inorganic substance can be activated and the reactivity of ammonia can be raised, and as a result, the successive reaction can be suppressed.

Although the invention is not restricted by the theory, it is considered that the carrier brings about an effect to enlarge the surface area of the rare earth element so as to utilize the expensive rare earth element effectively, and the activity and selectivity of the rare earth element is regulated according to the characteristics of the acid and/or base groups which the carrier has. Further, in the case of carriers having pores of the molecular order, such as SAPO, MeAPO and metallosilicates, particularly when those having a pore size of 0.45 to 0.7 nm are used, the formation of triethanolamine having branched structure can be suppressed due to so-called shape selectivity. Carriers having such a pore size include ZSM-5, ZSM-11, mordenite, ferrierite, SAPO-40, etc.

Alkylene oxides used as raw materials in the invention are alkylene oxides which have 2 to 4 carbon atoms, respectively and are represented by the general formula (I), and include, for example, ethylene oxide, propylene oxide, etc. Alkanolamines represented by the general formula (II) are obtained in correspondence to these raw material substances. Specific examples thereof are monoethanolamine, diethanolamine, triethanolamine, propanolamines, etc.

Since the reaction should be carried out in a liquid phase state, there is a necessity to hold the reaction pressure higher than the vapor pressure of the reaction mixture at the highest temperature inside the reactor.

The preparation of the alkanolamines can usually be carried out in the temperature range of 50° to 300° C. A preferred range therefor is 80° to 200° C. The operation pressure is 1 to 20 MPa.

The molar ratio of ammonia to the alkylene oxide is in the range of 1:1 to 40:1, preferably 1:1 to 20:1, more preferably 1:1 to 15:1.

Further, under the above conditions, a condition that the liquid hourly space velocity (LHSV) is 4 to 15 $h^{-1}$ or more is particularly advantageous for quantitative conversion of the alkylene oxide.

The catalyst of the invention has a high selectivity to monoalkanolamine formation, and thus can form an alkanolamine at a rate equal to that obtained by use of another solid catalyst, even at a ratio of ammonia to the alkylene oxide lower than that used in the case of said another solid catalyst. Moreover, as a result of the total amount of the feed raw materials decreasing, the apparatuses in the reaction system and recovery system can be made smaller, and the cost of equipment is reduced.

Preparation of ethanolamines from ethylene oxide and ammonia is chiefly illustrated in the following examples. These examples are intended for the purpose of description, and should not be interpreted to limit the invention.

LHSV, the conversion of ethylene oxide and the selectivity to monoethanolamine in the examples are defined as follows. Since products other than ethanolamines are hardly observed in each example, the conversion (mol %) of ethylene oxide is nearly equal to the total yield (mol %) of (mono, di and tri) ethanolamines based on ethylene oxide.

$$LHSV = \frac{\text{Volume of the liquid raw materials passing through the reactor per hour } (cm^3/hr)}{\text{Volume of the catalyst in the reactor } (cm^3)}$$

$$\text{Conversion of ethylene oxide} = \frac{\text{Mol number of ethylene oxide consumed by the reaction}}{\text{Mol number of the ethylene oxide feeded for the reaction}} \times 100 \ (mol\%)$$

$$\text{Selectivity to monoethanolamine} = \frac{\text{Weight of monoethanolamine in the product}}{\text{Weight of total ethanolamines in the product}} \times 100 \ (wt\%)$$

Examples of catalyst preparation

Catalyst A

This catalyst is an example in which lanthanum was used as the active component and ZSM-5 was used as the carrier.

50 g of ZSM-5 was added to 500 $cm^3$ of 1 mol/$dm^3$ aqueous lanthanum nitrate solution under stirring, the mixture was stirred at room temperature for 1 day, and after filtration, the cake was washed with 2 $dm^3$ of pure water. The cake was dried at 100° C. for 1 day and then pulverized to particle sizes of 0.1 to 0.2 mm to prepare a catalyst. The amount of lanthanum carried on the catalyst (in terms of the element) was 10% by weight.

Catalyst B

This catalyst is an example is which yttrium and silica were used as the active component and the carrier, respectively.

50 g of silica (CARiACT-50 produced by FUJI SILYSIA Chemical Co., Ltd.; spheres of 8 mesh or more) was packed into a basket-shaped vessel, and then the vessel was immersed for 5 hours in aqueous 18 wt % yttrium nitrate solution. The silica was pulled up from the solution, dried at 120° C. for 1 day and high temperature treated at 500° C. for 5 hours under an air stream. The product was pulverized into particle sizes of 0.1 to 0.2 mm to prepare a catalyst. The amount of yttrium carried on the catalyst was 7.8% by weight.

Catalyst C

This catalyst is an example in which yttrium and silica alumina were used as the active component and the carrier, respectively.

50 g of silica alumina (N631HN produced by Nikki Chemical Co., Ltd.; containing 25% of $Al_2O_3$) was packed into a basket-shaped vessel, and the vessel was immersed for 5 hours in aqueous 30 wt % yttrium nitrate solution. The resultant silica alumina was pulled up from the solution, dried at 120° C. for 1 day and high temperature treated at 500° C. for 5 hours under an air stream. The resultant product was pulverized into particle sizes of 0.1 to 0.2 mm to prepare a catalyst. The amount of yttrium carried on the catalyst was 7.8% by weight.

Catalyst D

This catalyst is an example in which lanthanum (heteropolyacid salt) and silica were used as the active component and carrier, respectively.

7.2 g of lanthanum nitrate hexahydrate and 42.7 g of 12-tungstophosphoric acid were dissolved in 300 $cm^3$ of pure water. 100 g of silica (CARiACT-50 produced by FUJI SILYSIA Chemical Co.; pulverized into 0.1 to 0.2 mm) was put in the solution, and the mixture was evaporated to dryness on a water bath. The residue was dried at 120° C. for 1 day and high temperature treated at 300° C. for 5 hours under an air stream to prepare a catalyst. The amount of lanthanum carried on the catalyst was 1.6% by weight.

Catalyst E

This catalyst is an example in which lanthanum and montmorillonite were used as the active component and carrier, respectively.

200 g of montmorillonite was added to 10 $dm^3$ of 0.05 mol/$dm^3$ aqueous lanthanum nitrate solution under stirring, the mixture was stirred at room temperature for 1 day and filtered, and the cake was washed with 10 $dm^3$ of pure water. The cake was dried at 100° C. for 1 day and pulverized into 200 mesh or less to give raw material powder for a catalyst.

An equal amount of pure water was added to 100 g of the powder. The mixture was kneaded by a kneader, dried at 100° C. for 1 day, and then high temperature treated at 500° C. for 5 hours under an air stream. The resultant solid matter was pulverized into particle sizes of 0.1 to 0.2 mm to give a catalyst. The amount of lanthanum carried on the catalyst was 14% by weight.

Catalyst F

This catalyst is an example in which yttrium and montmorillonite were used as the active component and carrier, respectively.

100 g of montmorillonite were added to 5 $dm^3$ of 0.05 mol/$dm^3$ aqueous yttrium nitrate solution under stirring, the mixture was stirred at room temperature for 1 day and filtered, and the cake was washed with 5 $dm^3$ of pure water. The cake was dried at 100° C. for 1 day and high temperature treated at 400° C. for 4 hours under an air stream. The resultant solid matter was pulverized into particle sizes of 0.1 to 0.2 mm to give a catalyst. The amount of yttrium carried on the catalyst was 10% by weight.

Catalyst G

This catalyst is an example in which ytterbium and saponite were used as the active component and carrier, respectively.

A catalyst was prepared in the same manner as in Catalyst F except that 0.05 mol/$dm^3$ aqueous ytterbium nitrate solution and saponite were used as the raw material of the rare earth element and the carrier, respectively. The amount of ytterbium carried on the catalyst was 18% by weight.

Catalyst H

This catalyst is an example in which cerium and montmorillonite were used as the active component and carrier, respectively.

A catalyst was prepared in the same manner as in Catalyst F except that 0.05 mol/$dm^3$ aqueous cerium nitrate solution was used as the raw material of the rare earth element. The amount of cerium carried on the catalyst was 18% by weight.

Catalyst I

This catalyst is an example in which lanthanum and yttrium, and montmorillonite were used as the active component and carrier, respectively.

A catalyst was prepared in the same manner as in Catalyst F except that a mixed aqueous solution comprising 0.025 mol of lanthanum nitrate and 0.025 mol of yttrium nitrate in 1 $dm^3$ of water was used as the raw material of the rare earth element. The amounts of lanthanum and yttrium carried on the catalyst were 7.5% by weight and 5% by weight, respectively.

Catalyst J

This catalyst is an example in which lanthanum and montmorillonite were used as the active ingredient and carrier, respectively.

A catalyst was prepared in the same manner as in Catalyst E except that 10 $dm^3$ of 0.05 mol/$dm^3$ aqueous lanthanum chloride solution was used in place of the aqueous lanthanum nitrate solution as the raw material of lanthanum. The amount of lanthanum carried on the catalyst was 14% by weight.

Catalyst K

This catalyst is an example in which lanthanum, iron and montmorillonite were used as the active component, addition metal and carrier, respectively.

A catalyst was prepared in the same manner as in Catalyst E except that 10 $dm^3$ of an aqueous solution comprising 0.025 mol of lanthanum nitrate and 0.025 mol of iron nitrate in 1 $dm^3$ of water was used as the raw material of lanthanum. The amounts of lanthanum carried on the catalyst was about 7% by weight.

Catalyst L

This catalyst is an example in which yttrium, aluminum and montmorillonite were used as the active component, addition metal and carrier, respectively.

A catalyst was prepared in the same manner as in Catalyst E except that 10 $dm^3$ of an aqueous solution comprising 0.025 mol of yttrium nitrate and 0.025 mol of aluminum nitrate in 1 $dm^3$ of water was used as the raw material of yttrium. The amounts of yttrium carried on the catalyst was about 5% by weight.

Catalyst M

This catalyst is an example in which lanthanum and montmorillonite were used as the rare earth element and carrier, respectively.

2 kg of montmorillonite was added to 100 $dm^3$ of 0.05 mol/$dm^3$ aqueous lanthanum nitrate solution under stirring, the mixture was stirred at room temperature for 1 day, and filtered. The cake was washed with 100 $dm^3$ of pure water, dried at 100° C. for 1 day, and pulverized into 200 mesh or less to give raw material powder (m) for a catalyst.

To 100 g of the rare material powder (m) for a catalyst were added 30 g of Avicel (crystalline cellulose produced by Asahi Chemical Co., Ltd.) and water in the same weight as the total of the weights of the raw material powder (m) for a catalyst and the Avicel. The mixture was kneaded, molded into pellets of diameter 0.5 mm and length 1 to 1.6 mm by an extrusion molder, dried at 100° C. for 1 day, and high temperature treated at 500° C. for 5 hours under an air stream to give a catalyst. The equivalent particle size of the catalyst was 1 to 1.6 mm. As to the catalyst, the volume of pores having a pore size of 10 nm to 10 μm was 0.26 cm$^3$/g. The pore volume was measured by the mercury porosimetry using high-pressure porosimeter (as is the same hereafter).

Catalyst N

A catalyst was prepared in the same manner as in Catalyst M except that the amount of Avicel to be used was made 60 g. The volume of pores having a pore size of 10 nm to 10 μm was 0.4 cm$^3$/g.

Catalyst O

A catalyst was prepared in the same manner as in Catalyst M except that the amount of Avicel to be used was made 100 g. The volume of pores having a pore size of 10 nm to 10 μm was 0.7 cm$^3$/g.

Catalyst P

A catalyst was prepared in the same manner as in Catalyst M except that 30 g of filter paper powder was added to 100 g of the raw material powder (m) for a catalyst, and the mixture was mixed and kneaded. The volume of pores having a pore size of 10 nm to 10 μm was 0.3 cm$^3$/g.

EXAMPLE 1

Catalyst A was packed into a stainless steel-made reactor of content volume 5.5 cm$^3$ and inside diameter 10.7 mm. Ammonia and ethylene oxide were fed, at constant velocities, into a reactor by the ascending method using a high pressure pump, and the reactor was heated in an oil bath. The reaction pressure was held to be 14 MPa. The reaction solution was sampled and the sample was analyzed by gas chromatography. The result is shown in Table 1.

EXAMPLES 2 to 14

Reaction was carried out in the same procedure as in Example 1 except that the catalyst and the reaction conditions were changed. The catalysts and reaction conditions used and reaction results are shown in Table 1. In Examples 5, 6 and 7, the same catalyst was used in change of the molar ratio of ammonia to ethylene oxide (NH$_3$/EO) in order to show how the product distribution changes according to the molar ratio.

TABLE 1

| Example | Catalyst | Active component | Carrier | NH$_3$/EO molar ratio | LHSV hr$^{-1}$ | Reaction temperature (°C.) | EO conversion (mol %) | Product distribution (wt %) | | |
|---|---|---|---|---|---|---|---|---|---|---|
| | | | | | | | | MEA | DEA | TEA |
| 1 | A | La | ZSM-5 | 15.0 | 12.8 | 106 | 98.5 | 69.8 | 28.7 | 1.5 |
| 2 | B | Y | silica | 10.8 | 11.5 | 115 | 97.6 | 63.6 | 26.0 | 8.5 |
| 3 | C | Y | silica alumina | 10.1 | 10.0 | 100 | 98.0 | 66.4 | 25.4 | 8.2 |
| 4 | D | La$^{a)}$ | silica | 12.1 | 12.8 | 105 | 98.5 | 68.3 | 26.1 | 5.6 |
| 5 | E | La | montmorillonite | 12.5 | 10.8 | 90 | 96.0 | 81.0 | 17.6 | 1.4 |
| 6 | E | La | montmorillonite | 4.8 | 10.1 | 80 | 98.0 | 62.8 | 31.4 | 5.8 |
| 7 | E | La | montmorillonite | 25.1 | 10.1 | 95 | 99.0 | 90.2 | 9.5 | 0.3 |
| 8 | F | Y | montmorillonite | 13.1 | 11.4 | 93 | 96.4 | 82.6 | 16.2 | 1.2 |
| 9 | G | Yb | saponite | 12.1 | 10.0 | 100 | 98.2 | 77.6 | 19.5 | 2.9 |
| 10 | H | Ce | montmorillonite | 11.8 | 11.5 | 98 | 96.6 | 81.2 | 17.4 | 1.4 |
| 11 | I | La, Y | montmorillonite | 11.1 | 10.0 | 102 | 98.5 | 77.8 | 19.2 | 2.9 |
| 12 | J | La | montmorillonite | 10.3 | 10.2 | 80 | 96.6 | 80.6 | 18.1 | 1.4 |
| 13 | K | La | montmorillonite | 12.2 | 10.1 | 85 | 98.6 | 78.8 | 18.5 | 2.7 |
| 14 | L | Y | montmorillonite | 12.1 | 10.2 | 85 | 98.6 | 80.5 | 18.1 | 1.4 |

MEA: monoethanolamine
EO: ethylene oxide
DEA: diethanolamine
TEA: triethanolamine
$^{a)}$heteropolyacid salt Catalyst Q A catalyst was prepared in the same manner as in Catalyst M except that 150 g of ammonium nitrate was added to 100 g of the raw material powder (m) for a catalyst, and the mixture was mixed and kneaded. The volume of pores having a pore size of 10 nm to 10 μm was 0.32 cm$^3$/g.

Comparative catalyst R

To 100 g of raw material powder (m) for a catalyst was added an equal amount of pure water. The mixture was kneaded by a kneader, molded into pellets of diameter 0.5 mm and length 2 to 5 mm by an extrusion molder, dried at 100° C. for 1 day, and then high temperature treated at 500° C. for 5 hours in the air to give a catalyst. As to the catalyst, the equivalent particle size was 1 to 1.6 mm, and the volume of pores having a pore size of 10 nm to 10 μm was 0.1 cm$^3$/g.

Examples of preparation of alkanolamines

The following comparative examples are examples in which heat-resisting inorganic substances, i.e. silica alumina, acid-activated clay and a carrier were used as catalysts.

Comparative example 1

Reaction was carried out in the same manner as in Example 1 except that silica alumina (N-631L produced by Nikki Chemical Co., Ltd.; containing 13% by weight of Al$_2$O$_3$; pulverized into 0.1 to 0.2 mm) was used in place of Catalyst A. Silica alumina is a representative one of so-called solid acid catalysts. The reaction conditions and the results are shown in Table 2. Although silica alumina is a strong solid acid, its activity and selectivity are low, and a great deal of triethanolamine was formed.

Comparative examples 2 and 3

Reaction was carried out in the same manner as in Example 1 except that activated clay powder (produced by Wako Pure Chemical Industries, Ltd.) was used in place of Catalyst A. Activated clay means so-called acid clay obtained by treating clay comprising montmorillonite as its main component with an acid, and is also a representative solid acid. The reaction conditions and the results are shown in Table 2.

Comparative example 4

Reaction was carried out in the same procedure as in Example 5 except that only montmorillonite carrying no rare earth element was used in place of Catalyst E. Since its activity is very low, the reaction temperature was greatly increased so that the same extent of the ethylene oxide conversion could be obtained. The montmorillonite has sodium ions at the ion exchange sites, and since it is not acid-treated, it was revealed by contacting it with wetted pH test paper that it is basic. The reaction conditions and the results are shown in the following Table 2. Since the montmorillonite does not carry a rare earth element as an active component, its selectivity is much inferior compared with Example 5.

bath. The pressure was held to be 14 MPa. The reaction solution was sampled and the sample was analyzed by gas chromatography. The reaction conditions and the results are shown in Table 3.

EXAMPLE 16 to 19

Reaction was carried out in the same procedure as in Example 15 except that the catalyst was changed to N, O, P and Q. The reaction conditions and the results are shown in Table 3.

Comparative example 5

Reaction was carried out in the same procedure as in Example 15 except that the catalyst was changed to R. This comparative example shows that, in the case of a catalyst having a large average particle size, where the volume of pores having a pore size of 10 nm to 10 μm is small, its catalytic activity and selectivity are lowered. Since its catalytic activity is low, reaction is carried out at a temperature higher than that in the corresponding example. The reaction conditions and the results are shown in Table 3.

TABLE 2

| Comparative Example | $NH_3/EO$ molar ratio | LHSV $hr^{-1}$ | Reaction temperature (°C.) | EO conversion (mol %) | Product distribution (wt %) | | |
|---|---|---|---|---|---|---|---|
| | | | | | MEA | DEA | TEA |
| 1 | 14.7 | 7.5 | 123 | 95.6 | 60.4 | 21.4 | 18.2 |
| 2 | 10.3 | 7.9 | 127 | 98.5 | 61.9 | 29.1 | 9.1 |
| 3 | 5.0 | 7.5 | 117 | 94.5 | 49.0 | 33.5 | 17.5 |
| 4 | 10.1 | 7.9 | 130 | 98.8 | 62.2 | 30.0 | 7.8 |

EO: ethylene oxide
MEA: monoethanolamine
DEA: diethanolamine
TEA: triethanolamine

EXAMPLE 15

Catalyst M was packed into a stainless steel tube reactor of content volume 5.5 cm³ and inside diameter 10.7 mm. Ammonia and ethylene oxide were fed, at a constant velocity, into the reactor according to the ascending method using a high pressure pump, and the reactor was heated in an oil

TABLE 3

| Example | Catalyst | Pore volume cm³/g | Particle size mm | $NH_3/EO$ molar ratio | LHSV $hr^{-1}$ | Reaction temperature (°C.) | EO conversion (mol %) | Product distribution (wt %) | | |
|---|---|---|---|---|---|---|---|---|---|---|
| | | | | | | | | MEA | DEA | TEA |
| Example 15 | M | 0.26 | 1–1.6 | 9.6 | 10.2 | 103 | 96.9 | 74.8 | 22.1 | 3.1 |
| Example 16 | N | 0.4 | 1–1.6 | 9.1 | 10.0 | 103 | 97.2 | 77.7 | 19.5 | 2.8 |
| Example 17 | O | 0.7 | 1–1.6 | 9.0 | 10.5 | 90 | 98.5 | 77.9 | 19.4 | 2.7 |
| Example 18 | P | 0.3 | 1–1.6 | 9.1 | 10.0 | 102 | 96.5 | 74.8 | 22.2 | 3.0 |
| Example 19 | Q | 0.32 | 1–1.6 | 8.9 | 10.1 | 103 | 97.2 | 74.5 | 22.3 | 3.2 |
| Comparative Example 5 | R | 0.1 | 1–1.6 | 10.2 | 10.2 | 120 | 91.0 | 70.8 | 24.7 | 4.5 |

EO: ethylene oxide
MEA: monoethanolamine
DEA: diethanolamine
TEA: triethanolamine

What is claimed is:

1. A process for preparation of an alkanolamine represented by the general formula (II)

wherein $R^1$, $R^2$, $R^3$ and $R^4$ each independently represent a hydrogen atom, a methyl group or an ethyl group, which comprises reacting an alkylene oxide represented by the general formula (I)

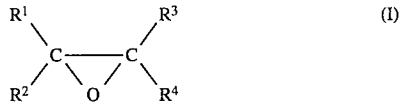

wherein $R^1$, $R^2$, $R^3$ and $R^4$ are the same as in the general formula (II),
with ammonia in a liquid phase at a mole ratio of ammonia to alkylene oxide of from 1:1 to 40:1, in the presence of a catalyst comprising a rare earth element supported on an inorganic heat-resisting carrier.

2. The process for preparation of an alkanolamine according to claim 1, wherein the inorganic heat-resisting carrier is an inorganic ion exchanger.

3. The process for preparation of an alkanolamine according to claim 2, wherein the inorganic ion exchanger is a layered silicate salt.

4. The process for preparation of the alkanolamine according to claim 1 wherein the catalyst is an inorganic solid catalyst having an average particle size of 0.3 mm or more comprising the rare earth element supported on an inorganic heat-resisting carrier in which the volume of pores having a pore size of 10 nm to 10 μm is 0.2 to 1 cm$^3$/g.

5. The process according to claim 1 wherein the rare earth element is supported in an amount of from 0.5 to 50% by weight of the carrier.

6. The process according to claim 1 wherein the catalyst further comprises an element selected from group consisting of Groups IVB, VB, VIB, VIIIB, VIII, III and IVA of the periodic table at an atomic ratio, with respect to the rare earth element, of 0 to 10.

7. The process of claim 1 wherein the alkylene oxide of formula (I) is ethylene oxide or propylene oxide.

8. The process of claim 1 which comprises carrying out the reaction of the alkylene oxide of formula (I) with ammonia in the liquid phase and a temperature in the range of from 50° to 300° C. and at a pressure of from 1 to 20 MPa.

9. The process of claim 8 wherein the temperature is from 80° to 200° C.

10. The process of claim 1 wherein the reaction between alkylene oxide and ammonia is carried out at a mole ratio of ammonia to alkylene oxide of from 1:1 to 20:1.

11. The process of claim 1 wherein the reaction between alkylene oxide and ammonia is carried out at a mole ratio of ammonia to alkylene oxide of from 1:1 to 15:1.

12. The process of claim 1 wherein the reaction between alkylene oxide and ammonia is carried out at a liquid hour space velocity in the range of from 4 to 15 h$^{-1}$.

13. The process of claim 1 wherein the rare earth element is lanthanum, yttrium, cerium or mixture thereof, and the inorganic heat-resisting carrier is montmorillonite.

* * * * *